United States Patent [19]

Akiyama

[11] Patent Number: 4,533,353
[45] Date of Patent: Aug. 6, 1985

[54] DRY TYPE DISCHARGE LIQUID EXTRACTION DEVICE FOR THE THORACIC CHAMBER

[75] Inventor: Sueshiro Akiyama, 4-41-6, Nishi-Tsutsujigaoka-Chofu, Tokyo, Japan, 182

[73] Assignees: Alex E. Genson; Brian S. Genson, both of Hewlett Harbor, N.Y.; Sueshiro Akiyama; Yoshihiro Akiyama, both of Tokyo, Japan

[21] Appl. No.: 399,904

[22] Filed: Jul. 19, 1982

[30] Foreign Application Priority Data

Apr. 8, 1982 [JP] Japan ................................. 57-57216

[51] Int. Cl.³ ............................................. A61M 1/00
[52] U.S. Cl. ..................................... 604/321; 137/205
[58] Field of Search ............................... 604/317–323; 137/205

[56] References Cited

U.S. PATENT DOCUMENTS

| | | | |
|---|---|---|---|
| 2,402,913 | 6/1946 | Poulter et al. | 137/526 |
| 3,363,626 | 1/1968 | Bidwell et al. | 128/276 |
| 3,363,627 | 1/1968 | Bidwell et al. | 128/276 |
| 3,683,913 | 8/1976 | Kurtz et al. | 128/276 |
| 4,105,031 | 8/1978 | Kurtz et al. | 604/321 |
| 4,324,244 | 4/1982 | Kurtz et al. | 128/276 |
| 4,372,336 | 2/1983 | Cornell et al. | 604/319 |
| 4,396,386 | 8/1983 | Kurtz et al. | 604/319 |
| 4,468,226 | 8/1984 | Kurtz et al. | 604/321 |
| 4,469,484 | 9/1984 | Kurtz et al. | 604/321 |

FOREIGN PATENT DOCUMENTS

| | | | |
|---|---|---|---|
| 096195 | 12/1983 | European Pat. Off. | 604/321 |
| 2082071 | 3/1982 | United Kingdom . | |

Primary Examiner—C. Fred Rosenbaum
Assistant Examiner—J. L. Kruter
Attorney, Agent, or Firm—Amster, Rothstein & Engelberg

[57] ABSTRACT

A dry type discharge liquid extraction apparatus is provided with a fluid collection chamber, a coupling for introducing a vacuum into the fluid collection chamber, and a pressure control valve for regulating the flow of air from the collection chamber to the coupling. Also provided is a one-way check valve between the fluid collection chamber and the pressure control valve and a vacuum pressure stabilizing valve which is vented to atmosphere and interposed between the pressure control valve and the coupling for selectively passing air at atmospheric pressure to stabilize the introduced vacuum.

12 Claims, 13 Drawing Figures

FIG. 2
FIG. 8
FIG. 9
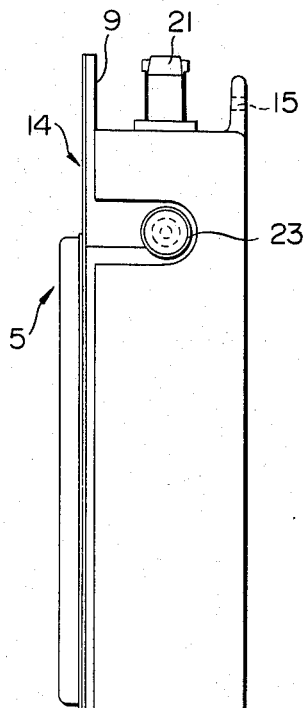
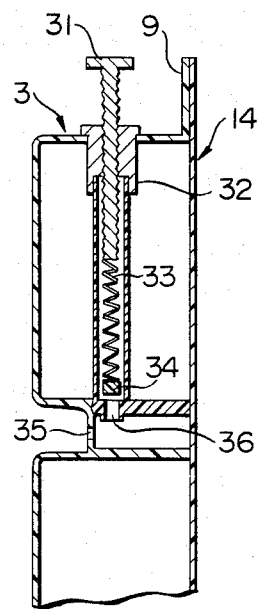
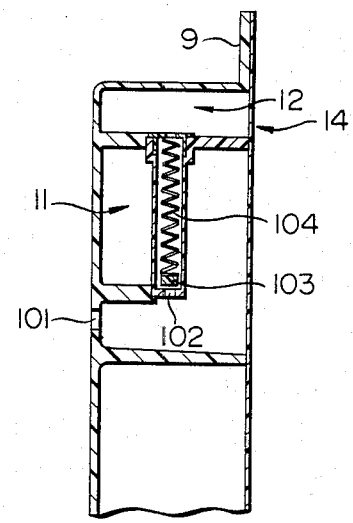
FIG. 10
FIG. 11
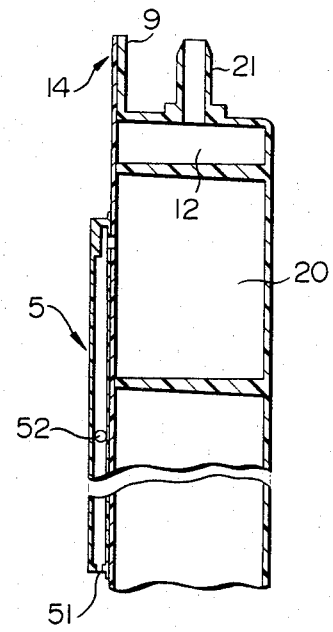
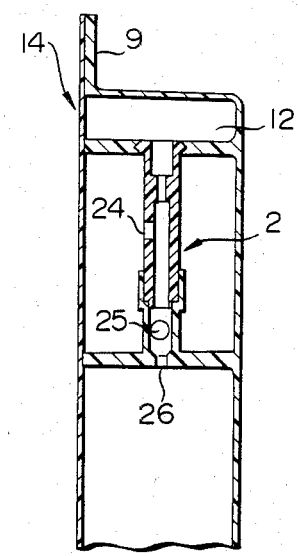

DRY TYPE DISCHARGE LIQUID EXTRACTION DEVICE FOR THE THORACIC CHAMBER

FIELD AND BACKGROUND OF THE INVENTION

This invention relates to a dry type discharge liquid extraction apparatus by means of which gases or liquids generated in a human body cavity after operation on a human body, particuarly thoracotomic operations, may be discharged for an extended time at a constant pressure.

The prior extraction apparatus used for discharging gases or liquids from the body cavity may be classified into the following two types. One is a wet type apparatus in which a suction pressure adjustment chamber having a liquid column is connected to a suction source for realizing a constant suction pressure. The other is a dry type apparatus provided with a suction pressure adjustment mechanism, in place of the suction pressure adjustment chamber having a liquid column, with the initially discharged liquid being stored in a sealing chamber for liquid sealing; or another dry type apparatus having no suction pressure adjustment function and connected to an adjustable suction source, with the initially discharged liquid being likewise stored in the liquid seal chamber for liquid sealing.

In a majority of the conventional wet type apparatus, there is provided a suction adjustment chamber and a liquid seal chamber to prevent reverse flow of the gas and liquid towards the body cavity, so that the extraction apparatus may be employed advantageously in a hospital room devoid of an adjustable suction source. However, such apparatus has the disadvantage that an accurate amount of liquid must be supplied to realize the water levels required in the suction adjustment chamber and the liquid seal chamber all at the busy time after the operation. In addition, when an elevated negative pressure is generated in the body cavity and the liquid in the seal chamber is sucked into the body cavity tube, provided that the elevated negative pressure in the body cavity is not decreased by some reason as in case of a valvular pneumothorax, the negative pressure acts continuously on the liquid sucked from the body cavity, so that the sucked liquid may remain in the tube. In such case, outside air may be passed through the liquid in the suction pressure adjustment chamber and discharged from the apparatus through the nozzle, so that discharge liquid cannot be extracted from the body cavity.

The conventional dry type extraction apparatus may be classified into two groups, with one having a suction pressure adjusting mechanism and making use of pneumatic pressure with the initially discharged liquid being stored so as to be used as sealing liquid. The extraction apparatus of this kind requires a complicated structure and a tube connection between the main member and the suction pressure adjusting mechanism provided outside of the main member. Accordingly, there is a necessity for providing positive sealing at each of the connecting portions. Since the liquid seal chamber is connected directly by a tube or the like to a body cavity tube, if an elevated negative pressure is generated in the body cavity, liquid may flow from the liquid seal chamber into the body cavity as reverse flow, thus occasionally destroying the liquid seal. If a slack exists in the body cavity tube, the reserved flow may remain in the lower part of the slack and operate as secondary manometer, thus causing changes in the suction pressure.

The other dry type apparatus is provided with no suction pressure adjusting mechanism and is instead connected to an outside adjustable suction source with the initally discharged liquid being used as sealing liquid in the liquid sealing chamber. In such case, there is the disadvantage that an adjustable suction source must be provided in the hospital chamber or a specified suction pressure adjusting mechanism must be annexed to the extraction apparatus. In such kind of extraction apparatus, there is again the risk of destruction of liquid extraction apparatus, there is again the risk of destruction of liquid sealing caused by reverse liquid flow from the liquid seal chamber into the body cavity caused by an elevated negative pressure in the body cavity and the secondary manometer phenomenon described above. In these two dry type extraction apparatus, a one-way ventilation valve is provided between the liquid sealing chamber and the suction source nozzle so as to be opened only in the direction of the suction source, and an elevated negative pressure is established in the body cavity. The problem of the liquid in the liquid sealing chamber remaining in the cavity tube and of the inhibition of suction is more severe than that in the wet type apparatus, because there is no air inlet from outside of the extraction apparatus by the operation of the one-way ventilation valve. Disadvantages common to the two existing dry type apparatus are that the allowable maximum levels of suction pressure and the negative pressure generated in the body cavity cannot be adjusted to accomodate the condition of the patient, and that the suction pressure is unstable in that it cannot adjust automatically with the unexpected fluctuations in the suction pressure occurring in the hospital piping system which may be in the range of, e.g., $-60$ to $-180$ cm. of water.

SUMMARY OF THE INVENTION

It is therefore a general object of the present invention to provide a dry type discharge liquid extraction apparatus free from the above mentioned disadvantages of both the prior wet and dry type discharge liquid extraction apparatus.

It is another object of the present invention to provide a dry type discharge liquid extraction apparatus in which the discharge liquid extraction operation can be started instantly without requiring complicated preparatory operation.

It is a further object of the present invention to provide a dry type discharge liquid extraction apparatus in which the suction pressure and the maximum allowable negative pressure established in the body cavity are adjustable and the suction pressure can be maintained steadily despite unforeseen fluctuations in the suction pressure in the hospital piping system.

It is a still further object of the present invention to provide a dry type discharge liquid extraction apparatus capable of single drain and double drain extraction of discharge liquid.

It is yet another object of the present invention to provide a dry type discharge liquid extraction apparatus capable of safely and promptly releasing incidental positive pressure in the body cavity for maintaining a constant negative pressure in the body cavity.

Other objects, features and advantages of the invention will be apparent from the following description of the preferred embodiment, especially when read in conjunction with the accompanying drawings.

BRIEF DESCRIPTION OF THE DRAWINGS

FIG. 2 is a side elevation thereof;

FIG. 8 is a sectional view taken along line IV—IV of FIG. 1;

FIG. 9 is a sectional view taken along line V—V of FIG. 1 and showing the suction pressure stabilizing valve;

FIG. 10 is a sectional view taken along line VI—VI of FIG. 1 and showing the flow meter;

FIG. 11 is a sectional view taken along line VII—VII of FIG. 1 and showing the suction pressure adjusting valve;

DETAILED DESCRIPTION OF THE DRAWINGS

Figure 1:
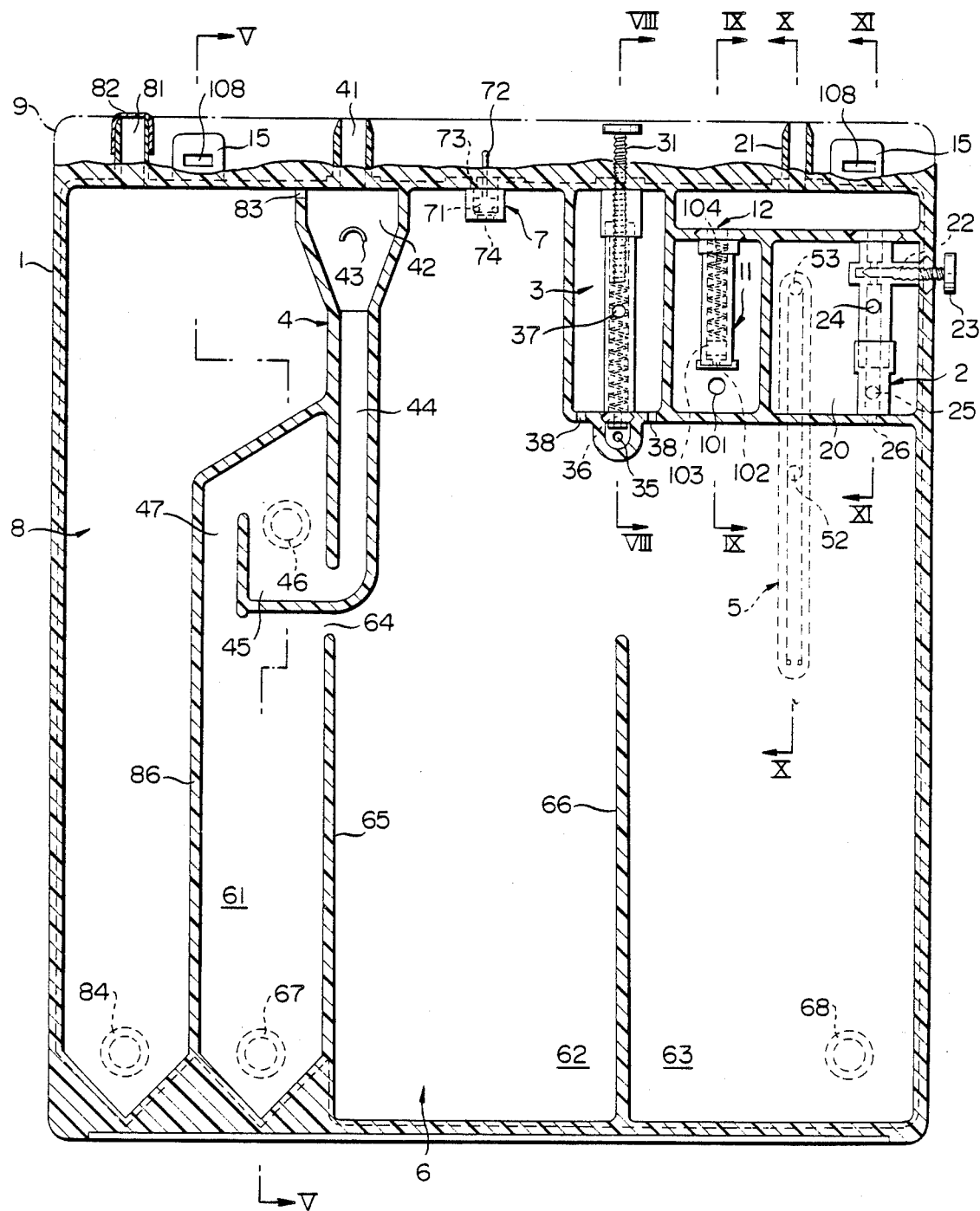
FIG. 1 is a front sectional view of the dry type discharge liquid extraction apparatus of the present invention.
Figure 3:
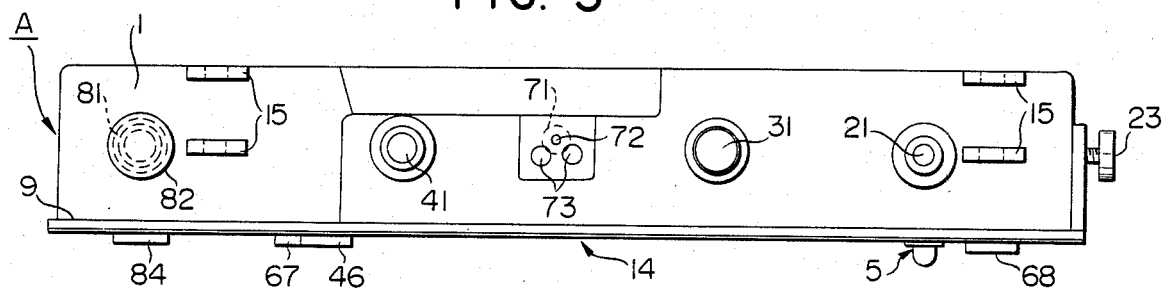
FIG. 3 is a plan view thereof.
Figure 4:
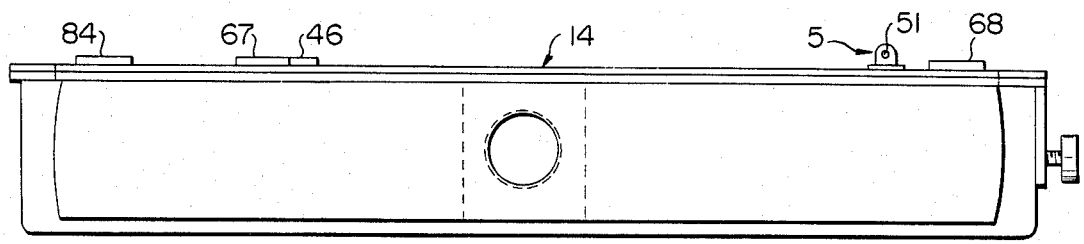
FIG. 4 is a bottom view thereof.

As shown in FIGS. 1 to 11, the dry type extraction apparatus of the present invention comprises generally a container A formed from a main member 1 of a plastic material opened at the front side as a single unit, and a flat transparent front plate 14 bonded airtightly with adhesive to the open front side of the main member 1.

The main member 1 includes a suction pressure adjusting chamber 12 at its upper portion, a suction pressure adjusting valve 2 communicating with the adjusting chamber 12, an adjusting valve 3 for adjusting the elevated negative pressure in the body cavity, a liquid seal chamber 4 connected to the body cavity, a positive/negative pressure release valve 7 for injecting and adjusting the positive/negative pressure in the apparatus, a suction pressure stabilizing valve 11 communicating with the adjusting chamber 12 and outside air, an auxiliary storage chamber 8 communicating with a liquid seal tube 4 and a main storage chamber 6 formed by a plurality of storage sections 61, 62, 63 communicating with each other. The main chamber 1 of the container A may be made of a transparent plastic as is the front plate 14. The storage sections may also be of any number and size as required for the particular applications.

Figure 12:
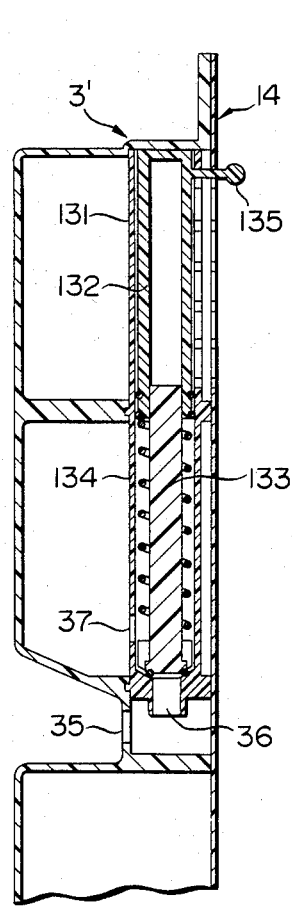
FIG. 12 is a sectional view in side elevation showing a modification of the elevated negative pressure adjusting valve.
Figure 13:
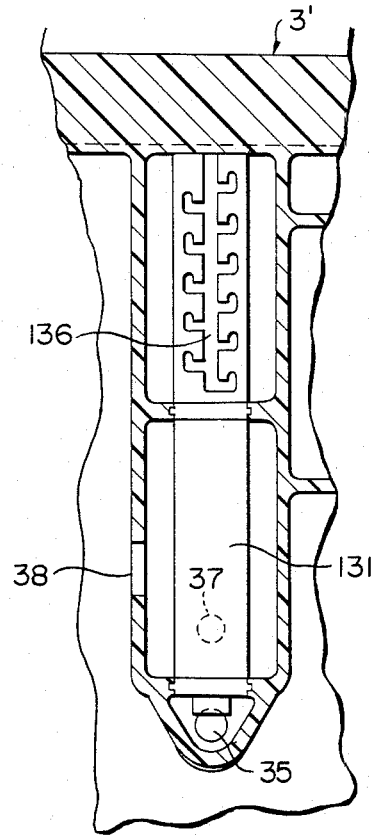
FIG. 13 is a front sectional view thereof.
Figure 5:
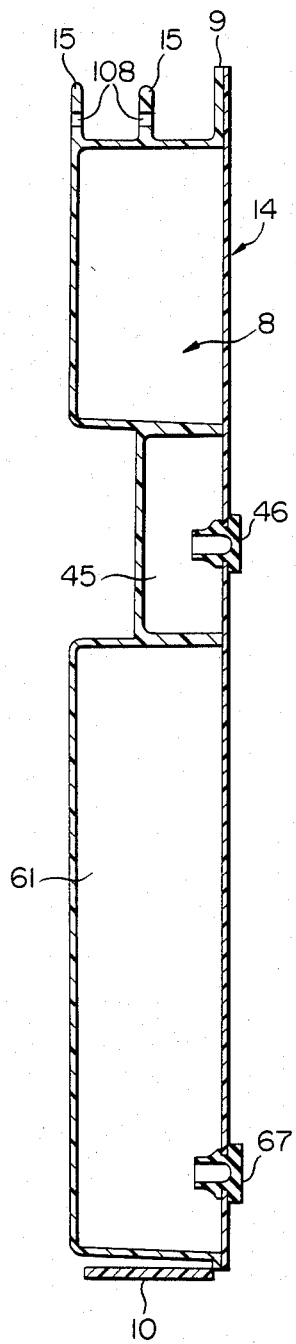
FIG. 5 is a sectional view taken along line I—I of FIG. 1.
Figure 6:
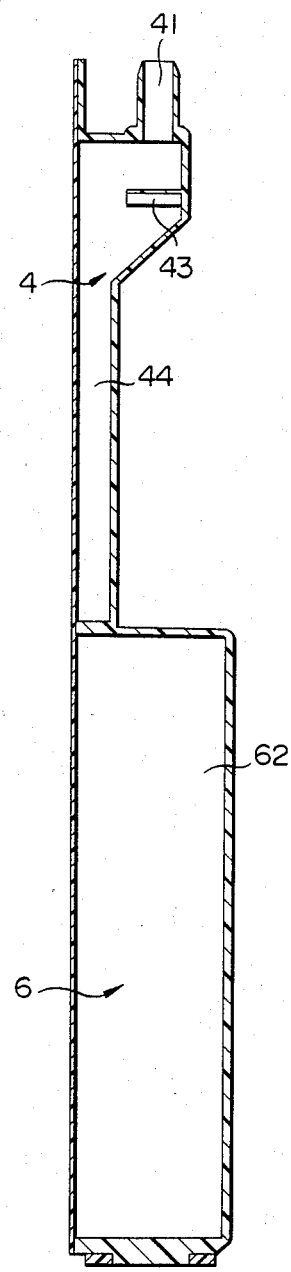
FIG. 6 is a sectional view taken along line II—II of FIG. 1.
Figure 7:
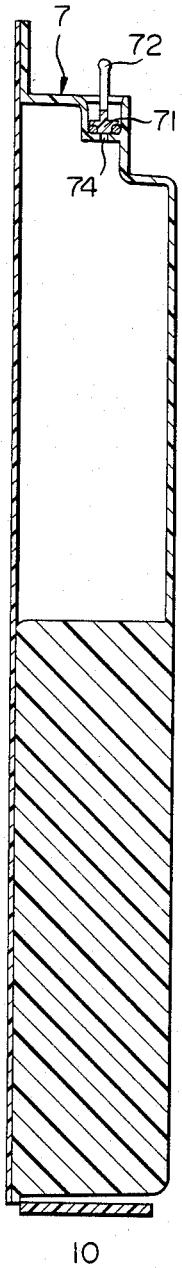
FIG. 7 is a sectional view taken along line III—III of FIG. 1.

A nozzle 21 connected to a suction source (not shown), a high negativity pressure adjusting screw 31, a negative pressure release knob 72, body cavity tube connection nozzles 41, 42 and a hanger rib 15 are provided protrudingly on the top wall of the main chamber 1 of the container A, and are protected by a master rib 9 from external impacts. The negative pressure adjusting valve 3 may be modified as shown in FIGS. 12 and 13 and provided with graduations or scales to permit the elevated negative pressure in the body cavity to be adjusted as desired. The nozzle 41 is adapted for connection to a body cavity tube (not shown) for directing gases or liquids generated in the body cavity to the present apparatus and leads into a flusher chamber 42. A sealing cap (not shown) is attached to a connector (not shown) at the end of the body cavity tube for protection from contact with outside air and intrusion of miscellaneous bacteria until use of the present apparatus. The flusher chamber 42 is in communication with the main storage chamber 6 by way of a negative pressure protection tube 44, a liquid sealing chamber 45 and an opening 47, and with the auxiliary storage chamber 8 through an opening 83. The main storage chamber 6 is also in communication with a positive/negative pressure release valve 7 through an opening 74, with the adjusting valve 3 through an opening 38 and a vent hole 37, and with adjusting valve 2 through an opening 26, respectively.

The gas or liquid introduced into the present apparatus from the body cavity through the body cavity tube and the nozzle 41 are directed into the liquid sealing chamber 45 through the flusher chamber 42 and the protection tube 44. The liquid sealing chamber 45 has a capacity such that the total stored liquid may be contained at a level lower than a reversal control projection 43 provided in the flusher chamber 42 so that, even in a case where the total liquid stored in the chamber 45 is raised in the flusher chamber 42 due to elevation of the negative pressure in the body cavity, a space can be maintained at all times between the rising liquid level and an opening 83 connecting to an auxiliary chamber 8 and a lower end opening of the nozzle 41. The liquid discharged initially from the body cavity is conveyed through the flusher chamber 42 and the protection tube 44 to the liquid sealing chamber 45 to be stored therein and used as sealing liquid. As discharge liquid is extracted and has reached a certain level above the lower end of tube 44, the discharged liquid thereafter starts to overflow into first storage section 61 of the main storage chamber 6 through the opening 47 for realizing a constant height of sealing liquid. When the lower end of the protection tube 44 of the tube 4 is positioned below the sealing liquid level, continuous foaming may take place from the bottom of the tube 44 through the liquid seal towards the opening 47. This indicates the occurrence of air leakage within the body cavity, provided that perfect air-tightness is maintained in the passage connecting to the body cavity. This phenomenon may be monitored easily through the transparent front plate 14. The liquid that may rise in the flusher chamber 42 from the bottom of tube 44 has a level difference of, e.g., more than 12 cm. Thus, in case of sealing failure due to breakage of some components of the present apparatus, other than the auxiliary chamber 8, the liquid stored in the liquid seal chamber 45 rises in and fills the tube 44 and the flusher chamber 42 to maintain a negative pressure in the body cavity of −12 cm. of water or higher. In case of using the present apparatus with a child patient undergoing abdominal respiration, sealing liquid may be moved up and down in the protection tube 44. Such movement of the liquid level may be monitored to know the status of the negative pressure in the patient's body cavity. Suitable graduations may be provided on the tube 4 from the bottom of the tube 44 to the maximum liquid level in the flusher chamber 42 as an aid in determining the negative pressure in the body cavity.

The overflow discharge liquid from the upper lip of the seal chamber 45 flows into the first storage section 61 through opening 47 to be stored therein. This first storage section 61 communicates through the upper opening 64 with the second and third section 62, 63 separated by the partitions 65, 66. The gas discharged from the body cavity is passed through the sealing tube 4, the opening 64 above the first storage section 61 of the main storage chamber 6, the opening 26, the valve 2 and the adjusting chamber 12 and discharged out the apparatus by way of nozzle 21. The liquid discharged initially from the body cavity is stored in the first storage section 61. The first storage section 61 has a narrow width and a small horizontal cross sectional area and hence may be provided with minute graduations whereby the initial discharge volume, critical for diagnosis, may be accurately read out as a function of elapsed time. The liquid seal chamber 45 is provided with a self sealing diaphragm 46 which can be pierced by a syringe needle during use to easily sample test liquid without obstructing the operation of the apparatus. In a case where the quantity of discharge liquid is extremely small and insufficient to fill the seal chamber 45 for liquid sealing, sterilized water may be injected for liquid sealing by a syringe needle which has pierced through the diaphragm 46. Another diaphragm 67 is provided in the lower portion of the first storage section 61 adapted to easily sample test liquid. The second and third section 62, 63 are of larger capacity for storage of overflow discharge liquid from the respective preceding sections, and can be provided with graduations whereby the total volume of the discharged liquid can be read out directly with respect to elapsed time. A self sealing diaphragm 68 is provided on the lower portion of the third storage section 63 which is adapted to be pierced by a syringe needle for injection of sterilized water for reducing the dead air space in the apparatus, or for extraction of the discharge liquid in excess of the capacity rating of the present apparatus.

The upper opening portion of the main storage chamber 6 is in communication with the suction pressure adjusting valve 2 through the opening 26 and the upper part of the adjusting valve 2 is in communication with the nozzle 21 through the suction pressure adjusting chamber 12. The adjusting valve 2 comprises a ventilation adjusting pin 22, a ventilation adjusting screw 23 and a one-way ventilation valve 25. A vent hole 53 is provided in a chamber 20 enclosing the adjusting valve 2 and a flow meter 5 is mounted for communication with the vent hole 53 and with the adjusting valve 2 through a vent hole 24 of the adjusting valve 2. A float ball 52 is provided for vertical movement in the flow meter 5 so that the screw 23 of the adjusting valve 2 may be operated while monitoring such vertical movement of the float ball 52 with the aid of graduations of the flow meter 5 for suitably setting suction pressure to a required value.

An adjusting valve 3 for adjusting the upper limit of negative pressure and a valve 11 for stabilizing suction pressure are provided adjacent to the adjusting valve 2 and the adjusting chamber 12. The purpose of the adjusting valve 3 is to adjust the negative pressure in the body cavity to a desired maximum allowable limit by the medium of the present apparatus. This valve 3 is provided in the open space above the second storage section 62 of the main storage chamber 6. The valve 3 comprises an adjusting screw 31, an air-tight washer 32, a spring 33, a closure valve 34, a suction port 35, and vent holes 36, 37 and communicates with the main storage chamber 6 through the opening 38 at the main chamber 1. The adjusting valve 3 also communicates with the adjusting valve 2 through the openings 38, 26, with the liquid seal tube 4 through the opening 38, and with the release valve 7 through the opening 74.

A modified embodiment of the adjusting valve 3 is shown in FIGS. 12 and 13 and has an outer sleeve 131 and an inner tube 132 slidable within the outer sleeve 131. The inner tube 132 has an upper knob 135 and is fitted with lower O-rings 132a and 132b. A stem 133 having the cross-sectional shape of a cross and being slidable within the inner tube 132 is also provided. An O-ring 133a is fitted to the lower end of the stem 133 for closing the vent hole 36. A spring 134 surrounds the stem 133 and urges the inner tube 132 upwards. Vent holes 37, 38 are provided for communication with the main storage chamber 6. The front plate 14 and the outer sleeve 131 are provided with a slit 136 with staggered branches, as shown and the knob 135 may be engaged in desired location in the slit 136 depending on the required setting of the negative pressure.

The suction pressure stabilizing valve 11 is provided between the adjusting valves 3 and 2 in communication with the chamber 12 and has a suction port 101 for suction of outside air, a vent hole 102 communicating with the vent hole 101, a normally closed valve 103 that is opened only when the suction pressure exceeds a predetermined range as, for example, a range from −60 to −70 cm. of water, and a spring 104 for maintaining the valve 103 normally closed. The purpose of the valve 11 is to supply a stabilized pressure to the adjusting valve 2 at all times through the adjusting chamber 12.

The positive/negative pressure release valve 7 is provided in the open space of the first storage section 61 of the main storage chamber 6 for communication through the opening 74 in the main member 1. The release valve 7 includes a valve body 71, a knob 72 extending upward from the valve body 71 and an upper vent hole 73 for communication with outside air.

The auxiliary storage chamber 8 of the extraction apparatus has an opening 83 in communication with the flusher chamber 42, an upper nozzle 81 for connection to a body cavity tube (not shown), and a lower diaphragm 84. The lower part of the auxiliary storage chamber 8 has a width and depth identical with that of the first storage section 61 of the main storage chamber 6 and the same function as that of the section 61 described above. Thus, when the discharge liquid is extracted in an amount in excess of the total capacity of the main storage chamber 6, the body cavity tube so far connected to the nozzle 41 is removed therefrom and connected to the nozzle 81 of auxiliary storage chamber 81 so that the extraction of the discharge liquid in excess of the capacity of the main storage chamber 6 may be continued without affecting the setting of suction pressure. The auxiliury storage chamber 8 enables the present apparatus to be used not only for single draining (e.g., extraction of discharge liquid only from the body cavity), but for double draining (e.g., both single draining and parallel draining or discharge liquid extraction from the upper body cavity or heart-sac under the same suction pressure). When employing the dry extraction apparatus for double draining, a nozzle cap 82 is removed from the nozzle 81 and a separate body cavity tube (not shown) is connected to the nozzle 81. A separate catheter (not shown) is attached to the end of this tube for insertion into the upper body cavity or heart-sac. The auxiliary storage chamber 8 is in communication with the flusher chamber 42 of the liquid seal tube 4 through the opening 83 and is subject to a suction pressure and other operating conditions identical to those for the main storage chamber 6. Since the auxiliary storage chamber 8 is divided from the main chamber 6 by a partition wall 86, the discharge liquid extracted from, for example, the upper body cavity or heart-sac may be stored separately and thus is usable as reference material critical for diagnosis. It is to be noted that the auxiliary storage chamber 8 may be omitted when the extraction apparatus is exclusively used for single draining.

At least one hanger rib 15 having a hanger hole 108 is provided at each side of the upper wall of the main member 1 of the container A, and the present apparatus may be hung vertically from a transverse girder of a bed by a band-like plastic hanger (not shown). Only two hanger ribs 15 may be provided at the center of the main member 1 or, alternatively, two more hanger ribs may be provided in addition to these central hanger ribs 15. When there is no object below the transverse rib, the present apparatus may be hung by the central hanger ribs 15 on the transverse girder. On the contrary, when there is an object, such as a vertical girder, below the transverse girder, the extraction apparatus may be hung by the rear side ribs. In such manner, the apparatus may be kept at all times in a vertical position for assuring safety and accuracy in the extraction operation. The requirement that the extraction apparatus be placed vertically below the body cavity of the patient, as required of any extraction apparatus, may be adapted with the aforementioned mounting of the extraction apparatus.

As best seen in FIG. 10, an openable floor stand 10 is provided at the bottom wall of the main member 1 of the container A so that the extraction apparatus may be placed on the floor adjacent to the patient's bed.

The dry extraction apparatus of the present invention is delivered to the hospital with the adjusting valves 2,3 and 11 adjusted in advance for realizing an accepted level of suction pressure. Thus, a safe and accurate extraction operation can be started without resorting to complicated preparatory operation, it being only necessary to connect a body cavity tube (not shown) provided with the extraction apparatus to a thoratic cavity catheter and to connect a suction tube (not shown) to a suction source.

In the dry extraction apparatus of the present invention, the body cavity tube connects from the patient's body cavity to the nozzle 41 which then connects by way of the liquid seal chamber 4, the opening 64 in the first storage section 61 of the main storage chamber 6, the upper part of the main storage chamber 6 and the opening 26 of the main member, to the suction pressure adjustment valve 2. The suction pressure adjustment valve 2 is opened towards the suction source when the air pressure prevailing from its one-way ventilation valve 25 to the cavity is higher than that prevailing from the one-way ventilation valve 25 to the suction source, and closed otherwise. Thus, the one-way ventilation valve 25 is always opened in the direction away from the suction source only and inhibits an air flow in the direction of the suction source. This one-way valve 25, operable to maintain the air pressure from the valve 25 to the body cavity at a negative pressure, acts with the liquid seal tube 4 to maintain negative pressure in the cavity. The one-way ventilation valve 25 of the dry extraction apparatus does not permit the air passage towards the cavity, in distinction from the liquid seal system of the customary wet extraction apparatus which makes use of water column pressure and provides two-way air passage through the sealing liquid towards the suction source and the body cavity. If the patient is in need of extreme negative pressure in the cavity, as when the lung is extremely contracted and must be expanded for recovery of breathing function, a sufficient negative pressure can be set in the body cavity with the dry extraction apparatus by the operation of the high negative pressure adjusting valve 3.

With the prior art dry extraction apparatus, unforeseen changes in the suction pressure prevailing in the piping system of the hospital in the range of $-60$ to $-180$ cm. of water may be highly inconvenient in arbitrarily setting the suction pressure required of the extraction apparatus and maintaining the suction pressure thus set accurately and over an extended time. With the wet extraction apparatus, suction pressure is set as water column pressure and is scarcely affected by fluctuations in the suction pressure in the piping system. On the contrary, the dry extraction apparatus is affected significantly by such fluctuations. Thus, for maintenance of a stable suction pressure, special means must be used so that the function of the suction pressure adjusting valve in the extraction apparatus may be brought into full play despite fluctuations in the suction pressure in the piping system.

With the dry extraction apparatus of the present invention, the suction pressure stabilizing valve 11 has the normally closed valve 103 that is opened only in cases where predetermined suction pressure is exceeded. Thus, when the suction pressure in the piping system has increased beyond the predetermined suction pressure, outside air is sucked into the adjusting chamber 12 through the suction opening 101 and the vent hole 102 for counter-balancing the elevation in the suction pressure. In this way, the air pressure experienced by the suction pressure adjusting valve 2 is restricted at all times to its design setting range so that the operational reliability of the flow meter 5 may be assured notwithstanding significant fluctuations in the suction pressure in the piping system. In setting the maximum allowable range of the negative pressure in the cavity with the dry extraction apparatus of the present invention, a cap is removed from an end connector (not shown) of a suction tube (not shown) and attached in advance to the nozzle 21. The extraction apparatus is then connected to an outlet of the suction source. The screw 23 is then loosened to bring the pin 22 to its fully open position, the spring 33 of the adjusting valve 3 is compressed to its innermost position, and the vent hole 36 is hermetically closed by the normally open valve 34. A body cavity tube (not shown) connecting to the patient's body cavity, is then clamped to the nozzle 41. After termination of the above preparatory operation, the air remaining in the extraction apparatus is discharged from the apparatus through the adjusting valve 2, the chamber 12 and the nozzle 21 by the operation of the suction motor, so that the negative pressure in the extraction apparatus is now increased. When the negative pressure in the dry extraction apparatus has increased sufficiently as evidenced by floating of the float ball 52 of the flow meter 5 to its uppermost position, the spring 33 of the adjusting valve 3 is gradually loosened. As the spring force of the spring 33 is lowered gradually until it is no longer able to resist the elevated negative pressure in the extraction apparatus, the normally closed valve 34 is opened and outside air invades into the extraction apparatus through the suction opening 35, vent holes 36, 37 and the opening 38 to release the elevated negative pressure in the apparatus. This decreased negative pressure thus lowered acts on flow meter 5 through the opening 26 so that the float ball 52 descends from its uppermost position. The force of the spring 33, that is, the force acting in opposition to the negative pressure load of the extraction apparatus, can be monitored on the basis of the vertical position of the float ball 52. Thus, by operation of the high negative pressure adjusting valve 3, it is possible to adjust the force of the spring 33 and to control the timing and volume of air suction through the suction opening 35 until the negative pressure is stabilized to an operating range as required by the float ball 52. The maximum allowable negative pressure in the extraction apparatus, and hence in the body cavity, can be set as desired by thus adjusting the force of the spring 33 to an optimum level.

In addition, if a positive pressure appears suddenly in the extraction apparatus for some reason, as when the patient has coughed and inhaled a lot of air and hence the pressure in the body cavity has changed from negative to positive, such positive pressure may be released promptly out of the apparatus by the valve body 71 of the positive/negative pressure release valve 7. As long as negative pressure is maintained in the extraction apparatus, the valve body 71 of the release valve 7 is attracted towards the inside of the extraction apparatus for closing the opening 74 and preventing the invasion of outside air. When the pressure in the extraction apparatus has switched to positive, the valve body 71 is raised outwards for prompt recovery of the negative pressure within the extraction apparatus.

Especially with both dry and wet extraction apparatus of the prior art, when an elevated negative pressure in excess of a preset suction pressure is generated in the body cavity and such pressure is not decreased for some reason as in cases of valvular pneumothorax, the liquid stored in the liquid seal chamber is sucked into the body cavity tube but is not lowered, so that the continuous extraction of the discharge liquid from the body cavity is no longer feasible. Since one-way ventilation valves have been provided in a majority of the conventional dry extraction apparatus which open only in the direction of the suction source, such negative pressure could not be released and hence the ability of liquid extraction might be affected more severely than in the case of the wet extraction apparatus. Such elevated negative pressure could not be dissolved unless outside air was injected into the extraction apparatus or the body cavity through a syringe needle which pierces through the body cavity tube or the diaphragm.

According to the dry extraction apparatus of the present invention, such state may be dissolved by manually gripping the release knob 72 and raising upwardly the valve body 71, the opening 74 thus being opened to permit entrance of outside air into the extraction apparatus through the vent hole 32 to promptly release the elevated negative pressure in the body cavity through the liquid seal tube 4. In this case, a level difference of more than 12 cm. is maintained between the lower end of the protection tube 44 and the highest level of the liquid rising in the flusher chamber 42, so that a negative pressure in excess of a normal value is always maintained in the body cavity for assuring safe operation.

As hereinabove described, with the dry extraction apparatus of the present invention, discharge liquid extraction can be initiated for an ordinary patient without the necessity of performing complicated preparatory operation. For a patient requiring a special adjustment of the negative pressure in the body cavity, both the suction pressure and the maximum allowable negative pressure in the body cavity may be set as desired. Stable suction pressure may be always maintained despite unforeseen changes in the suction pressure in the piping system. Discharge liquid extraction can be made by single drain or double drain technique for both adult and pediatric patients. Any positive pressure occasionally appearing in the body cavity may be released promptly through the extraction apparatus for assuring a safe operation. In case of generation of an extreme negative pressure in the body cavity, it may be released promptly to permit the continued extraction operation. There is no risk of the reverse flow of the discharged liquid towards the body cavity, and the negative pressure in excess of a minimum level of −12 cm. water may be assured irrespective of the presence or absence of suction load, while the changes in the negative pressure in the body cavity and the air leakage in the body cavity can be monitored.

In addition thereto, the dry extraction apparatus of the present invention can be made as a highly airproofed unitary structure composed of a container proper and a flat and transparent front plate. Suitable graduations may be provided to the front plate for indicating the liquid level and/or suction pressure in the respective chambers or sections of the extraction apparatus, or suitable recording space may be placed on the front plate for recording the data to be used as diagnostic reference.

What is claimed is:

1. A dry tape discharge liquid extraction apparatus for a thoracic procedure comprising:
   a container having a main body opened at the front side including,
      a suction pressure adjusting chamber formed at the upper portion thereof and provided with a nozzle for connection to a suction source,
      a liquid seal tube provided with a liquid seal chamber and a nozzle for connection to a human body cavity tube, and
      a main storage chamber in communication with a liquid seal chamber of said liquid seal tube, and
      a front plate secured on the front opened side of the main body,
   the container being provided with,
      a suction pressure adjusting valve means in communication with said suction pressure adjusting chamber and said main storage chamber,
      a high negative pressure adjusting valve means for adjusting excess pressure in the human body cavity,
      a valve means for releasing positive and negative pressure in said container, and
      a suction pressure stabilizing valve in communication with said suction pressure adjusting chamber and outside air.

2. A dry tape discharge liquid extraction apparatus as claimed in claim 1 wherein: the liquid seal tube further includes a flusher chamber and a reversal control projection.

3. A dry type discharge liquid extraction apparatus as claimed in claim 1, wherein:
   the high negative pressure adjusting valve comprises an outer sleeve, an inner tube slidable within said outer sleeve and having a knob engagable with staggered branches of a slit on said outer sleeve, a stem slidable within the inner tube, and a spring surrounding the stem to force the inner tube upwardly.

4. A dry type discharge liquid extraction apparatus as claimed in claim 1, wherein: the suction pressure stabilizing valve for supplying a stabilized pressure to the suction pressure adjusting valve means comprises a normally closed valve member and a spring for maintaining said valve member normally closed.

5. A dry type discharge liquid extraction apparatus as claimed in claim 1, wherein:
the valve means for releasing positive and negative pressure comprises a valve body, a knob extending upwardly from said valve body, and an upper vent hole in communication with outside air.

6. A dry type discharge liquid extraction apparatus comprising:
a fluid collection chamber,
coupling means for introducing a vacuum into said fluid collection chamber,
a pressure control valve assembly for regulating the flow of air from said collection chamber to said coupling means, and comprising a ventilation adjusting pin, a ventilation adjusting screw and a one-way ventilation valve,
a one-way check valve interposed between the said fluid collection chamber and said pressure control valve operative to pass air from the said fluid collection chamber to said coupling means, while preventing reverse flow therebetween, and
vacuum pressure stabilizing valve means vented to atmosphere interposed between said pressure control valve means and said coupling means for selectively passing air at atmospheric pressure to stabilize the introduced vacuum.

7. A dry type discharge liquid extraction as claimed in claim 6, further comprising:
a high negative pressure adjusting valve for adjusting high negative pressure in the body cavity.

8. A dry type discharge liquid extraction apparatus as claimed in claim 7, wherein:
the high negative pressure adjusting valve comprises an adjusting screw, an air-tight washer, a spring and a closure valve.

9. A dry type discharge liquid extraction apparatus as claimed in claim 7, wherein:
the high negative pressure adjusting valve comprises an outer sleeve, an inner tube slideable within said outer sleeve and having a knob engageable with staggered branches of a slit on said outer sleeve, a stem slideable within said inner tube, and a spring surrounding the stem to force the inner tube upwardly.

10. A dry type discharge liquid extraction apparatus as claimed in claim 6, further comprising:
a positive/negative pressure release valve for releasing and adjusting positive/negative pressure in said fluid collection chamber.

11. A dry type discharge liquid extraction apparatus as claimed in claim 10, wherein:
the positive/negative pressure release valve comprises a valve body, a knob extending upwardly from said valve body, and an upper vent hole in communication with air at atmospheric pressure.

12. A dry type discharge liquid extraction apparatus as claimed in claim 6, wherein:
the vacuum pressure stabilizing valve means comprises a valve member and a spring for maintaining said valve member normally closed.

* * * * *